US009622760B2

(12) United States Patent
Brandt et al.

(10) Patent No.: US 9,622,760 B2
(45) Date of Patent: Apr. 18, 2017

(54) ORTHOPEDIC JIG, PIN, AND METHOD

(71) Applicant: Stryker Leibinger GmbH & Co. KG, Freiburg (DE)

(72) Inventors: Matt Brandt, Chicago, IL (US); Amir Sarvestani, Freiburg (DE)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 0 days.

(21) Appl. No.: 14/607,616

(22) Filed: Jan. 28, 2015

(65) Prior Publication Data

US 2015/0142001 A1 May 21, 2015

Related U.S. Application Data

(62) Division of application No. 11/714,567, filed on Mar. 6, 2007, now abandoned.

(51) Int. Cl.
*A61B 17/58* (2006.01)
*A61B 17/17* (2006.01)
*A61B 17/15* (2006.01)
*A61B 17/00* (2006.01)

(52) U.S. Cl.
CPC ............. *A61B 17/17* (2013.01); *A61B 17/15* (2013.01); *A61B 2017/00862* (2013.01); *A61B 2017/00951* (2013.01)

(58) Field of Classification Search
CPC . A61B 17/17; A61B 17/1717; A61B 17/1721; A61B 17/1725; A61B 17/15
USPC ................ 606/86 R–89, 91, 96, 104, 70–71, 606/270–321; 144/253.91, 28.8–28.9; 135/25.4; 24/13; 411/347–349
See application file for complete search history.

(56) References Cited

U.S. PATENT DOCUMENTS

| | | | |
|---|---|---|---|
| 3,592,250 A | 7/1971 | Petroshanoff | |
| 4,335,715 A | 6/1982 | Kirkley | |
| 4,759,671 A * | 7/1988 | Duran | F16B 21/086 411/347 |
| 4,846,162 A | 7/1989 | Moehring | |
| 4,848,327 A | 7/1989 | Perdue | |
| 5,163,940 A | 11/1992 | Bourque | |
| 5,405,349 A | 4/1995 | Burkinshaw et al. | |
| 5,704,941 A * | 1/1998 | Jacober | A61B 17/157 606/87 |
| 5,722,978 A | 3/1998 | Jenkins, Jr. | |
| 5,931,621 A * | 8/1999 | Griffith | F16B 39/02 411/255 |

(Continued)

FOREIGN PATENT DOCUMENTS

| | | |
|---|---|---|
| DE | 19811354 | 9/1999 |
| DE | 10340434 | 4/2004 |

(Continued)

*Primary Examiner* — Matthew Lawson
(74) *Attorney, Agent, or Firm* — Howard and Howard Attorneys PLLC

(57) ABSTRACT

An orthopedic jig and pins therefore are disclosed that allow the pins to be pre-loaded into apertures through the jig before the jig is positioned at a desired location with respect to a bone during an orthopedic surgical procedure. At least one of the pin and/or jig includes a retention mechanism whereby the pin can be inserted into the bore and releasably restrained therein until the jig is place is the selected position and the pins driven into the bone.

8 Claims, 2 Drawing Sheets

(56) References Cited

U.S. PATENT DOCUMENTS

| | | | |
|---|---|---|---|
| 5,931,838 A * | 8/1999 | Vito | A61B 17/8047 |
| | | | 606/281 |
| 6,030,389 A | 2/2000 | Wagner et al. | |
| 6,224,594 B1 | 5/2001 | Luboshitz et al. | |
| 6,241,748 B1 | 6/2001 | Adams | |
| 6,379,360 B1 * | 4/2002 | Ackeret | A61B 17/1725 |
| | | | 606/60 |
| 7,066,943 B2 | 6/2006 | Zirkle, Jr. | |
| 7,104,991 B2 * | 9/2006 | Dixon | A61B 17/1728 |
| | | | 606/279 |
| 7,166,114 B2 | 1/2007 | Moctezuma de la Barrera et al. | |
| 7,785,327 B1 | 8/2010 | Navarro et al. | |
| 2003/0216742 A1 * | 11/2003 | Wetzler | A61B 17/17 |
| | | | 606/96 |
| 2004/0158147 A1 | 8/2004 | Shifrin | |
| 2005/0096657 A1 | 5/2005 | Autericque et al. | |
| 2005/0158147 A1 * | 7/2005 | Baus | F16B 21/125 |
| | | | 411/347 |
| 2005/0234467 A1 | 10/2005 | Rains | |
| 2005/0261701 A1 | 11/2005 | McGuire et al. | |
| 2006/0004398 A1 | 1/2006 | Binder et al. | |
| 2006/0030852 A1 * | 2/2006 | Sevrain | A61B 17/68 |
| | | | 606/328 |
| 2006/0200147 A1 | 9/2006 | Ensign et al. | |
| 2007/0078483 A1 | 4/2007 | Ewaschuk et al. | |
| 2007/0173837 A1 | 7/2007 | Chan et al. | |
| 2008/0234692 A1 | 9/2008 | Brandt et al. | |
| 2009/0228043 A9 | 9/2009 | Egli et al. | |

FOREIGN PATENT DOCUMENTS

| | | |
|---|---|---|
| DE | 102005002939 | 9/2006 |
| DE | 102006034590 | 2/2007 |
| DE | 602004000771 | 5/2007 |
| EP | 1719468 | 12/2004 |
| EP | 1832239 A1 | 9/2007 |
| JP | 09-075366 A | 3/1997 |
| JP | 2001-212151 A | 8/2001 |
| JP | 2003-010215 A | 1/2003 |
| JP | 2003339727 * | 12/2003 |
| WO | 2008016628 | 2/2008 |

* cited by examiner

ORTHOPEDIC JIG, PIN, AND METHOD

CROSS REFERENCE TO RELATED APPLICATIONS

This application is a divisional of U.S. patent application Ser. No. 11/714,567, filed Mar. 6, 2007, the entire content of which is hereby incorporated by reference.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates to surgical instruments.

2. Description of the Background of the Invention

In orthopedic surgery, pins are regularly used to temporarily affix jigs, such as cutting blocks, to the bone. A standard technique for affixing a jig to a bone is for a surgeon to hold the jig to the bone, carefully insert the pins through apertures in the jig, and then drive the pins into the bone through the holes in order to achieve the fixation. The number of pins needed for affixing each jig varies typically between two and four, and often two or more jigs need to be temporarily affixed to the bone. Consequently, sometimes ten or more pins need to be inserted to the jigs and drilled into the bone during a surgical procedure. This pin insertion process must be done very carefully by the surgeon in order to avoid pin jamming or stripping and can take up to several seconds or longer for each pin. As a result, the total time for pinning can add several minutes or more to a surgical procedure requiring a larger number of jigs.

SUMMARY OF THE INVENTION

According to one aspect of the invention, a pin for use with an orthopedic jig includes a shaft adapted to slide through an aperture associated with the jig and a restraining member disposed on the shaft. The restraining member is adapted to releasably hold the pin within the aperture.

According to another aspect of the invention, an orthopedic jig in combination with a pin includes a jig body defining an aperture therethrough, a pin disposed through the aperture, and a restraining member associated with at least one of the jig body and the pin. The restraining member releasably restrains the pin within the aperture prior to fixation to a support surface.

According to yet another aspect of the invention, a jig adapted for fixation to a bone with a pin during an orthopedic surgical procedure includes a body, an aperture associated with the body and adapted to receive the pin therethrough, and a retention mechanism adapted to releasably restrain the pin in the aperture.

According to a further aspect of the invention, a method of attaching a jig to a bone during a surgery includes the steps of releasably securing a pin within a bore defined by a jig using a retention mechanism associated with one of the jigs and the pin at a location removed from the bone, engaging the jig with the bone, and driving the pin into the bone.

Other aspects and advantages of the present invention will become apparent upon consideration of the following detailed description of the drawings in which like numbers are used to designate similar structures in various embodiments.

DETAILED DESCRIPTION

Figure 1:
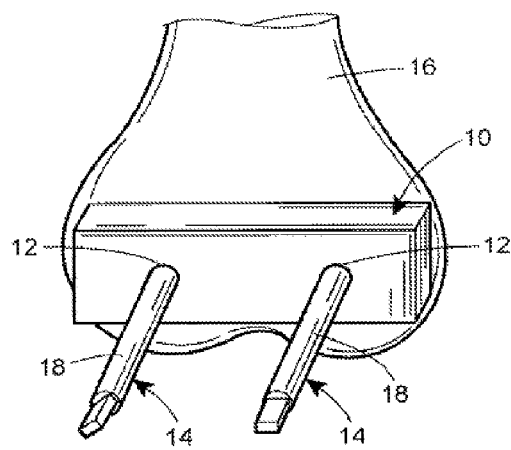
FIG. 1 is a fragmentary schematic isometric view of an orthopedic jig pinned to a bone according to one aspect of the present invention.

With reference to FIG. 1, a jig 10 for use in orthopedic surgical procedures includes apertures, such as through bores 12, for receiving pins 14 therethrough for attaching the jig 10 to a work surface, such as a bone 16 during the surgical procedure. The pins 14 are releasably secured in the bores 12, such as by adhesive, clamping, and/or locking action, prior to attachment to the bone 16 by a restraining member associated with at least one of the jig 10 and the pin 14 so that the pins 14 may be pre-loaded within the bores 12 in an area away from the surgical procedure by one person and subsequently engaged with the bone 16 with the pre-loaded pins already releasably held within the bores 12 by another person during the surgical procedure. Preferably, the restraining member is disposed and adapted so that an end of the pin 14 that is to be inserted into the bone is releasably retained within the bore 12, although in other embodiments the restraining member may be adapted to releasably retain the pin in other selected orientations in the aperture. Thereafter, a shaft 18 of each pin 14 may be driven through the bore 12 into the bone 16 by any appropriate method, such as drilling, screwing, or hammering, for example, to secure the jig 10 in a selected orientation with respect to the bone.

Figure 2:
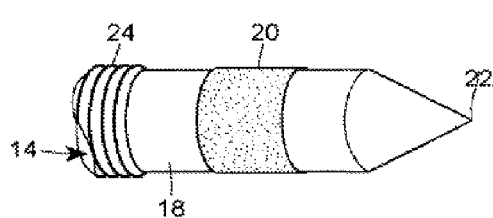
FIG. 2 is a fragmentary isometric view of a pin according to another aspect of the present invention.
Figure 3:
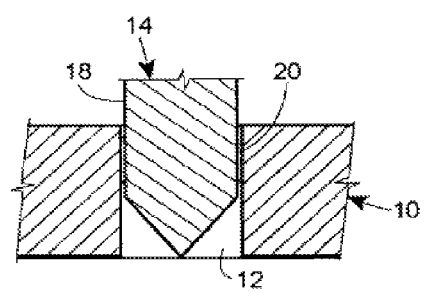
FIG. 3 is a fragmentary cross-sectional view of a the pin of FIG. 2 pre-loaded into an aperture through a jig.

FIGS. 2 and 3 show one embodiment in which the restraining member is associated with a pin 14. In this embodiment, the restraining member comprises a film of adhesive 20 disposed around a peripheral surface of the shaft 18 of the pin 14, as best shown in FIG. 2. When the shaft 18 is inserted into the bore 12, the adhesive 20 adheres lightly to the inner surface of the bore 12, which is smooth in this embodiment, whereby the pin is releasably retained in the bore until the pin is driven into the bone 16 by any normal method. The adhesive 20 is preferably disposed near an end 22 of the shaft 18 that is adapted for being driven into the bone 16, such as by an insertion tip, so that the end 22 will reside within the aperture 12, as shown in FIG. 3. The adhesive 20 may be applied immediately before the pin 14 is to be used, or the pin may be pre-formed to include a film of adhesive and include, for example, a removable cover strip (not shown) to protect the adhesive from unwanted debris during storage. The pin 14, in one embodiment, may include threads 24 along the shaft 18 to facilitate screwing into the bone 16. In other embodiments, the shaft may be smooth, have other relief, such as grooves or ridges (not shown), or include other features desired for a particular use.

Figure 4:
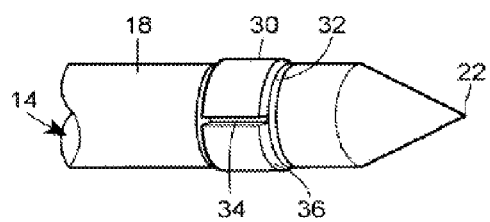
FIG. 4 is a fragmentary isometric view of a pin according to another aspect of the present invention.
Figure 5:
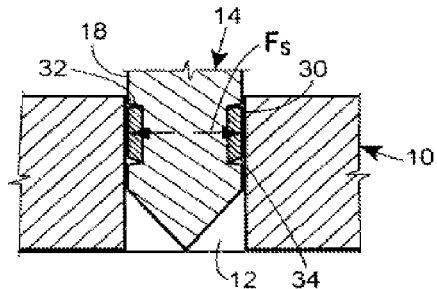
FIG. 5 is a fragmentary cross-sectional view of the pin of FIG. 4 pre-loaded into an aperture through a jig.

Turning now to the embodiment shown in FIGS. 4. and 5, the pin 14 carries a resilient member, such as a tension ring 30, that frictionally engages the inner surface of the bore 12 to releasably restrain the pin in the bore. The tension ring 30 is disposed in an outer peripheral groove 32 that circumscribes the shaft 18 near the end 22. When the tension ring 30 is in a relaxed state, the outer diameter extends radially beyond the surface of the shaft 18 and has a larger diameter than a minimum diameter of the bore 12, and the inner diameter is disposed inside the outer peripheral groove 32 so that tension ring 30 does not fall off the shaft. A radial gap 34 allows the tension ring 30 to resiliently contract and expand. The outer peripheral groove 32 has a depth sufficient to allow the tension ring 30 to be constricted so as to be received within the bore 12. In one embodiment, the outer peripheral groove 32 has a depth sufficient to allow the tension ring 30 to be completely disposed therein such that the outside diameter of the tension ring is substantially coextensive with the diameter of the shaft 18 adjacent the outer peripheral groove. Thereby, the shaft 18 and the tension ring 30 may be inserted into a bore 12 having an inside diameter substantially equal to the diameter of the shaft, and the tension ring resiliently urges outward against the interior surface of the bore with a force Fs to releasably retain the end 22 of the pin in the bore by clamping action until the pin is driven into the bone 16. In one embodiment, the tension ring 30 includes a tapered leading edge 36, which may facilitate driving the end 22 and the tension ring 30 directly into the bone 16 and also facilitate retaining the pin in the bone thereafter.

Figure 6:
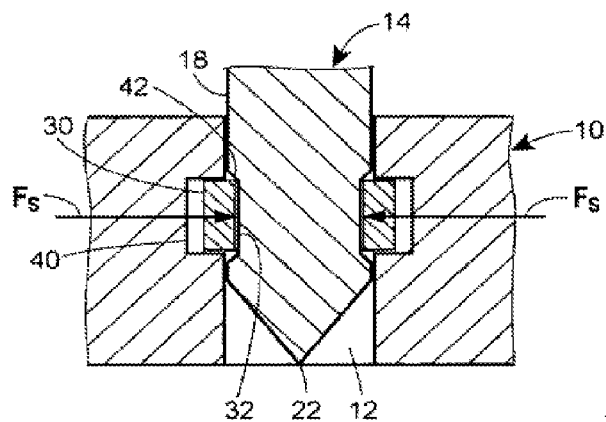
FIG. 6 is a fragmentary cross-sectional view of a jig and pin according to a further aspect of the present invention.

FIG. 6 shows an embodiment in which the restraining member is associated with the jig 10. In this embodiment, a tension ring 30 is disposed in an inner peripheral groove 40 that is defined completely around the inner surface of the bore 12. In a relaxed state, the outside diameter of the tension ring 30 is larger than the inside diameter of the bore 12, and the inside diameter of the tension ring is smaller than the outside diameter of the shaft 18 of the pin 14. The inner peripheral groove 40 has a depth sufficient to allow the tension ring 30 to expand enough to receive the shaft 18 of the pin 14 therethrough, and in one embodiment, the inner peripheral groove is at least as deep as a thickness of the tension ring. Thereby, the tension ring 30 is normally carried by the jig 10, and when the pin 14 is inserted into the bore 12, the tension ring resiliently expands around the shaft 18 and frictionally grips the shaft with a spring force Fs to releasably retain the end 22 of the pin in the bore by clamping action. In one embodiment, the shaft 18 may also include an outer peripheral groove 32 having at least a tapered trailing edge 42 adapted to receive the tension ring 30, thereby allowing the tension ring to releasably lockingly engage the pin at the outer peripheral groove in addition or alternative to clamping.

Figure 7:
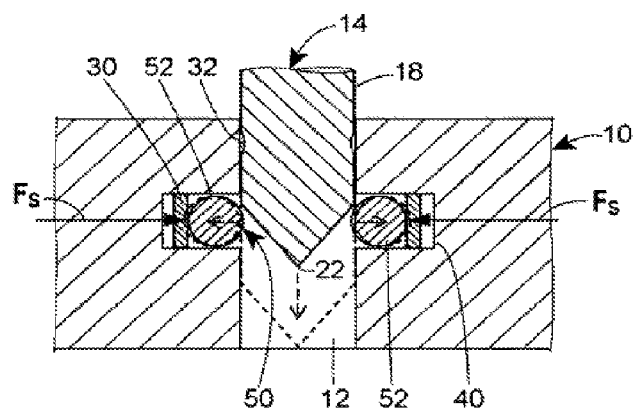
FIG. 7 is a fragmentary cross-sectional view of a jig and pin according to yet another aspect of the present invention.

FIG. 7 shows another embodiment in which the restraining member is associated with the jig 10. In this embodiment, a ball plunger 50 carried by the jig 10 is disposed in the bore 12 to releasably restrain the shaft 18 of the pin 14 therein by clamping and/or locking. In one embodiment, the ball plunger 50 includes one or more ball members 52 that are resiliently urged, such as with a tension ring 30, into the bore 12 from one or more recesses, such as an inner peripheral groove 40, in the inner surface of the bore. In a relaxed state, the ball members 52 protrude into the bore 12. When the pin 14 is inserted into the bore, the ball members 52 press resiliently against the shaft to releasably restrain the end 22 of the shaft in the bore by clamping. In one embodiment, the shaft 18 may be smooth, and in another embodiment, the shaft 18 also may include a recess, such as a shallow outer peripheral groove 32, located and adapted to receive a portion of the ball members 52 therein and provide an additional resilient locking mechanism for releasably retaining the pin 14 in the bore 12 in addition or alternative to clamping.

Figure 8:
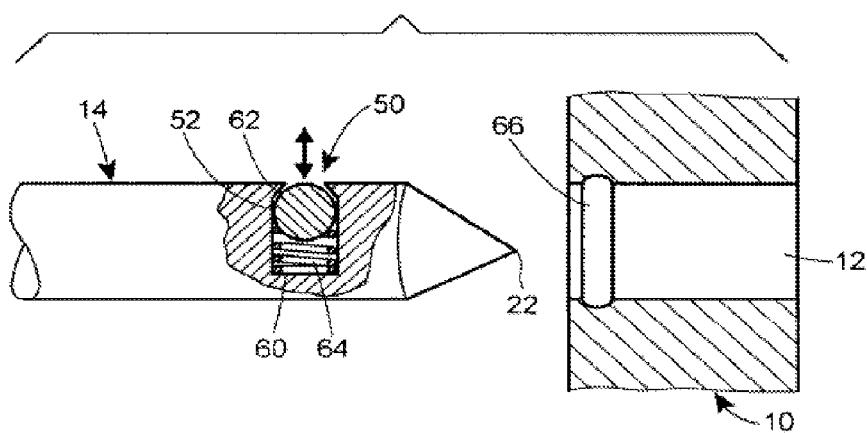
FIG. 8 is a fragmentary side view of a jig and pin according to a still further embodiment of the present invention with portions shown cutaway and in cross-section for clarity.

In FIG. 8, another embodiment is shown in which the pin 14 includes resilient retention mechanism, such as a ball plunger 50, to resiliently engage the bore 12 through the jig 10 in order to retain the pin in a desired preloaded position within the bore. The ball plunger 50 includes a ball member 52 disposed in a blind bore 60 that extends generally transversely to a longitudinal axis of the pin. The blind bore 60 has an opening through an exterior surface of the pin through which a portion of the ball member 52 extends to engage the bore 12 of the jig. A narrowed neck 62 portion of the bore retains the ball member 52 inside the blind bore 60, and a resilient member, such as a spring 64, urges the ball member radially outwardly. Preferably, the ball plunger 50 is located near the tip 22 of the pin 14 so that the tip of the pin is retained within the bore 12 of the jig 10, but in other embodiments, the ball plunger may be located anywhere along the length of pin. When the tip 22 of the pin 14 is inserted into the bore 12 of the jig 10, the spring 64 presses the ball member 52 resiliently against the bore 12, which retains the pin inside the bore 12. The bore 12 of the jig 10 may be smooth or the bore 12, in which case the ball plunger 50 simply clamps the pin inside the bore 12, or the bore may include a receiving recess for the ball plunger 50, such as an inner peripheral groove 66, to releasably lockingly engage the pin 14 in a pre-loaded position within the bore 12 in addition or alternative to clamping. In the embodiment shown in FIG. 8, the pin 14 has a single locked pre-loaded position. Other embodiments may include additional ball plungers 50 located at other locations along the length of the pin 14 and/or additional grooves 66 along the length of the bore 12 to provide multiple locked and/or clamped preloaded positions.

The jig 10 and pins 14 disclosed herein allow a method of attaching the jig to a bone during a surgery. In one possible method of affixing any one of the jigs 10 disclosed herein to a bone 16, a scrub nurse may pre-load the appropriate pins 14 to the appropriate jig 10, i.e., insert the insertion end 22 of the pin into the bore 12, before the surgical procedure or otherwise away from the immediate temporal or physical vicinity of the incision or wound through which the jig will be affixed to the bone 16. Subsequently, the pre-loaded jig 10 with the pins 14 releasably restrained in the bores 12 may be given to the surgeon, for example, at the time when required for fixation to the bone 16. The surgeon may then position the jig 10 with the pre-loaded pins 14 at a selected position with respect to the bone 16 through the incision or wound and then drive the pins 14 through the bore 12 into the bone in an appropriate manner. If a surgical navigational system (not shown) is being used during the procedure, the jig 10 and/or pins 14 may be adapted for integration and use therewith during the affixation procedure.

INDUSTRIAL APPLICABILITY

The present invention may be useful at least in orthopedic surgical procedures. By allowing the pins 14 to be preloaded to a jig 10 by the surgeon or by someone other than the surgeon during an orthopedic surgical procedure, the devices and methods disclosed herein may, in some circumstances, reduce the time needed by the surgeon during a surgical procedure to affix a jig to a patient, thereby possibly reducing the overall time and cost of the surgical procedure over prior jigs and methods of attachment. Other industrial applications are also possible.

Numerous modifications to the present invention will be apparent to those skilled in the art in view of the foregoing description. In addition, all possible combinations and subcombinations of the embodiments disclosed herein are specifically contemplated and expressly included in the scope of the present disclosure. Accordingly, this description is to be construed as illustrative only and is presented for the purpose of enabling those skilled in the art to make and use the invention and to teach the best mode of carrying out same. The exclusive rights to all modifications that come within the scope of the impending claims are hereby reserved.

What is claimed is:

1. A method of attaching a jig to a bone during a surgery, the method comprising the steps of:
    providing a surgical orthopedic pin with a shaft and a restraining device separate from and carried by the shaft, the restraining device comprising a resilient member that is compressible to press radially outwardly from the shaft;
    providing a cutting jig with a bore;
    driving the surgical orthopedic pin into the bone from a first, inoperative position outside the bone, at which the restraining device is disposed within a bore of the jig, and compressing the restraining device in a radial direction at the first position, to a second, operative position in the bone spaced from the first position, in which the pin holds the jig to the bone; and
    retracting the surgical orthopedic pin out of the bone from the second, operative position in the bone so as to loosen the jig.

2. The method of claim 1, including the step of releasably securing the pin within the bore defined by the jig using the restraining device associated with the pin at a location removed from the bone.

3. The method of claim 1, including the step of releasably locking the pin in the bore.

4. The method of claim 1, including the step of using the pin in conjunction with a surgical navigation system.

5. The method of claim 1, wherein the step of providing the pin includes providing the restraining device as an adhesive carried by the pin.

6. The method of claim 1, wherein the step of providing the pin includes providing the resilient member as a tension ring.

7. The method of claim 1, wherein the step of providing the pin includes providing the restraining device as a ball plunger.

8. The method of claim 1, wherein the step of providing is performed by a first person, and wherein the step of driving is performed by at least a second person.

* * * * *